(12) United States Patent
Konkle et al.

(10) Patent No.: US 7,078,232 B2
(45) Date of Patent: *Jul. 18, 2006

(54) ADIPOSE TISSUE-DERIVED ADULT STEM OR STROMAL CELLS FOR THE REPAIR OF ARTICULAR CARTILAGE FRACTURES AND USES THEREOF

(75) Inventors: Jon Konkle, Durham, NC (US); Jeffrey M. Gimble, Baton Rouge, LA (US)

(73) Assignee: Artecel, Inc.

( * ) Notice: Subject to any disclaimer, the term of this patent is extended or adjusted under 35 U.S.C. 154(b) by 567 days.

This patent is subject to a terminal disclaimer.

(21) Appl. No.: 10/713,906

(22) Filed: Jan. 14, 2003

(65) Prior Publication Data

US 2004/0166096 A1    Aug. 26, 2004

Related U.S. Application Data

(63) Continuation-in-part of application No. 10/125,106, filed on Apr. 18, 2002, now Pat. No. 6,841,150, which is a continuation of application No. 09/573,989, filed on May 17, 2000, now Pat. No. 6,429,013.

(60) Provisional application No. 60/149,850, filed on Aug. 19, 1999.

(51) Int. Cl.
*C12N 5/00*    (2006.01)

(52) U.S. Cl. .................. 435/377; 435/325; 435/366; 435/395; 424/93.21; 424/93.7

(58) Field of Classification Search ............. 435/377, 435/325, 366, 395, 455; 424/93.7, 93.21
See application file for complete search history.

(56) References Cited

U.S. PATENT DOCUMENTS

| | | | |
|---|---|---|---|
| 4,362,567 A | | 12/1982 | Schwarz et al. |
| 4,377,572 A | | 3/1983 | Schwarz et al. |
| 5,160,490 A | | 11/1992 | Naughton et al. |
| 5,197,973 A | | 3/1993 | Pang et al. |
| 5,486,359 A | | 1/1996 | Caplan et al. |
| 5,723,331 A | | 3/1998 | Tubo et al. |
| 5,786,207 A | | 7/1998 | Katz et al. |
| 5,863,531 A | | 1/1999 | Naughton et al. |
| 5,902,741 A | | 5/1999 | Purchio et al. |
| 5,908,784 A | | 6/1999 | Johnstone et al. |
| 6,153,432 A | * | 11/2000 | Halvorsen et al. .......... 435/377 |
| 6,194,203 B1 | | 2/2001 | Blum et al. |
| 6,200,606 B1 | | 3/2001 | Peterson et al. |
| 6,429,013 B1 | * | 8/2002 | Halvorsen et al. .......... 435/377 |
| 6,841,150 B1 | * | 1/2005 | Halvorsen et al. .......... 424/93.7 |

FOREIGN PATENT DOCUMENTS

| | | |
|---|---|---|
| FR | 2 448 900 | 9/1980 |
| FR | 2 448 901 | 9/1980 |
| WO | WO95/33821 A1 | 12/1995 |
| WO | WO99/28444 A1 | 6/1999 |
| WO | WO00/53795 A1 | 9/2000 |

OTHER PUBLICATIONS

Ashton et al., "Formation of Bone and Cartilage by Marrow Stromal Cells in Diffusion Chambers *in Vivo*," Clin. Orthop. Rel. Res., (1980), vol. 151, pp. 294-307.

Ballock & Reddi, "Thyroxine is the Serum Factor That Regulates Morphogenesis of Columar Cartilage from Isolated Chondrocytes in Chemically Defined Medium," J. Cell Biol., (1994), vol. 126:5, pp. 1311-1318.

Benya, P., et al., Dedifferentiated Chondrocytes Reexpress the Differentiated Collagen Phenotype When Cultured in Agarose Gels, Cell, 30 (1982), 215-224.

Bonadio et al., "Localized, Direct Plasmid Gene Delivery *in Vivo*: Prolonged Therapy Results In Reproducible Tissue Regeneration," Nat. Med., (1999), vol. 5, pp. 753-759.

Bruder et al., "Osteochondral Differentiation and the Emergence of State-Specific Osteogenic Cell-Surface Molecules by Bone Marrow Cells in Diffusion Chambers," Bone Mineral, (1990), vol. 11, pp. 141-151.

U.S. Appl. No. 60/123,711, filed Mar. 10, 1999, Peterson et al.

U.S. Appl. No. 60/162,462, filed Oct. 29, 1999, Peterson et al.

Burris et al., "A Novel Method for Analysis of Nuclear Receptor Function at Natural Promoters: Peroxisome Proliferator-Activated Receptor y Agonist Actions on a P2 Gene Expression Detected Using Branched DNA Messenger RNA Quantitation," Molecular Endocrinology, (1999), 13, 3, 410.

(Continued)

*Primary Examiner*—Leon B. Lankford, Jr.
(74) *Attorney, Agent, or Firm*—Drinker Biddle & Reath LLP (57) ABSTRACT

The invention provides cells, methods and compositions based upon the use of adipose tissue-derived adult stem cells in the repair of articular cartilage fractures or defects. The invention is useful in providing a treatment of articular cartilage fractures in a clinical setting.

19 Claims, 4 Drawing Sheets

OTHER PUBLICATIONS

Byk T. et al., "Lipofectamine and Related Cationic Lipids Strongly Improve Adenoviral Infection Efficiency of Primitive Human Hematopoietic Cells," Human Gene Therapy, (1998), vol. 9, pp. 2493-2502.

Chu CR et al., "Articular Cartilage Repair Using Allogeneic Perichondrocyteseeded Biodegradable Porous Polylactic Acid (PLA): A Tissue-Engineering Study," J. Biomed. Mater. Res., (1995), vol. 29, pp. 1147-1154.

Dennis et al., "Osteogenesis in Marrow Derived Mesenchymal Cell Porous Ceramic Composites Transplanted Subcutaneously: Effect of Fibronectin and Laminin on Cell Retention and Rate of Osteogenic Expression," Cell Transpl. (1991), vol. 1, pp. 23-32.

Dorheim et al., "Osteoblastic Gene Expression During Adipogenesis in Hematopoietic Supporting Murine Bone Marrow Stromal Cells," J. Cell Physiol., (1993), vol. 154, pp. 317-328.

Elmer et al., "Immunohistochemical Localization of Cyclic AMP During Normal and Abnormal Chick and Mouse Limb Development," Teratology, (1981), vol. 24, pp, 215-223.

Gimble, Jeffrey Martin, "The Function of Adipocytes in the Bone Marrow Stroma," The New Biologist, (1990), 2, 4, 304.

Gimble et al., "Adipogenesis in a Myeloid Supporting Bone Marrow Stromal Cell Line," J. Cell Biochem., (1992), vol. 50, pp. 73-82.

Gimble et al., "The Function of Adipocytes in the Bone Marrow Stroma: An Update," Bone, (Nov. 1996), vol. 19:5, pp. 421-428.

Gimble et al., "Nuclear Hormone Receptors and Adipogenesis," Critical Reviews in Eukaryotic Gene Expression, (1998), 8(2), 141.

Gimble et al., "Adipocyte Biology of the Bone," Adipocyte Biology and Hormone Signaling, IOS Press, The Netherlands, (2000), 231.

Goshima et al., "The Origin of Bone Formed in Composite Grafts of Porous Calcium Phosphate Ceramic Loaded with Marrow Cells," Clin. Orthop. Rel. Res., (1991), vol. 269, pp. 274-283.

Gronthos et al., "Surface Protein Characterization of Human Adipose Tissue-Derived Stromal Cells," Journal of Cellular Physiology, (2001), 9999,1.

Hauschka, S. D., "Clonal Analysis of Vertebrate Myogenesis III. Developmental Changes in the Muscle-Colony-Forming Cells of the Human Fetal Limb," Development Biology, (1974), vol. 37, pp. 345-368.

Hendrickson DA et al., "Chondrocyte-Fibrin Matrix Transplants for Resurfacing Extensive Articular Cartilage Defects," Orthop. Res., (1994), vol. 12, pp. 485-497.

Ichinose et al., "Structure of Transglutaminases," J. Biol. Chem., (1990), vol. 265:3, pp. 13411-13414.

Kato et al., "Terminal Differentiation and Calcification in Rabbit Chondrocyte Cultures Grown in Centrifuge Tubes: Regulation by Transforming Growth Factor β and Serum Factors," PNAS, (1988), vol. 85, pp. 9552-9556.

Mackay et al., (1998), Tissue Engineering 4:415-428.

Mayne et al., "Changes in Type of Collagen Synthesized as Clones of Chick Chondrocytes Grown and Eventually Lose Division Capacity," PNAS, (1976), vol. 73:5, pp. 1674-1678.

Mayne et al., "Changes in the Synthesis of Minor Cartilage Collagens after Growth of Chick Chonrocytes in 5-Bromo-2'-Deoxyuridine or to Senscence," Exp. Cell. Res., (1984), vol. 151:1, pp. 171-182.

Mizuno, M.D., Hiroshi, "The Myogenic Potential of Human Processed Lipoaspirates—Part I: Morphological, Immunohistochemical Analysis and Gene Expression," J. Jpn. P.R.S., (2001), 21 427.

Mizuno et al., "Myogenic Differentiation by Human Processed Lipoaspirate Cells," Plastic and Reconstructive Surgery, (2002), 109, 1, 199.

Nakahara et al., "*In Vitro* Differentiation of Bone and Hypertrophic Cartilage from Periosteal-Derived Cells," Exp. Cell Res., (1981), vol. 195, pp. 492-503.

Oegama et al., "Characterization of a Hyaluronic Acid-Dermatan Sulfate Proteoglycan Complex from Dedifferentiated Human Chondrocyte Cultures," J. Biol. Chem., (1981) vol. 256:2, pp. 1015-1022.

Okayama et al., "Differences Among Sulfated Proteoglycans Synthesized in Nonchondrogenic Cells, Presumptive Chondroblasts, and Chondroblasts," PNAS, (1976), vol. 73:9, pp. 3224-3228.

Pacifici et al., "Transformation of Chondroblasts by Rous Sarcoma Virus and Synthesis of the Sulfated Proteoglycan Matrix," Cell, (1977), vol. 4, pp. 891-899.

Pacifici et al., "12-O-Tetradecanoylphorbol-13-acetate-induced Changes in Sulfated Proteoglycan Synthesis in Cultured Chondroblasts," Cancer Res., (1980), vol. 40:7, pp. 2461-2464.

Pacifici et al., "Changes in the Sulfated Proteoglycans Synthesized by "Aging" Chondrocytes," J. Biol. Chem., (1981), vol. 256:2, pp. 1029-1037.

Perka C. et al., "Matrix-Mixed Culture: New Methodology for Chondrocyte Culture and Preparation of Cartilage Transplants," J. Biomed. Mater. Res., (2000), vol. 49, pp. 305-311.

Phinney et al., "Plastic Adherent Stromal Cells from the Bone Marrow of Commonly Used Strains of Inbred Mice: Variation in Yield, Growth, and Differentiation," J. Cell Biochem., (1999), vol. 72:4, pp. 570-585.

Remy-Martin et al., "Vascular Smooth Muscle Differentiation of Murine Stroma: A Sequential Model," Exp. Hematol., (1999), vol. 27.12, pp. 1782-1795.

Saladin et al., "Differential Regulation of Peroxisome Proliferator Activatec Receptor y 1 (PPARy1) and PPARy2 Messenger RNA Expression in the Early Stages of Adipogenesis[1]" Cell Growth & Differentiation, (1999), 10, 43.

Sechriest VF. et al., "GAG-Augmented Polysaccharide Hydrogel: A Novel Biocompatible and Biodegradable Material to Support Chondrogenesis," J. Biomed. Mater. Res., (2000), vol. 49, pp. 534-541.

Solursh et al., "Stage- and Position-Related Changes in Chondrogenic Response of Chick Embryonic Wing Mesenchyme to Treatment with Dibutyryl Cyclic AMP," Development Biology, (1981), vol. 83, pp. 9-19.

Solursh, "Formation of Cartilage Tissue In Vitro," J. Cell Biochem., (1991), vol. 45, pp. 258-260.

Sommer B. et al., "Efficient Gene Transfer into Normal Human Skeletal Cells Using Recombinant Adenovirus and Conjugated Adenovirus-DNA Complexes," Calif. Tissue Int., (1999), vol. 64, pp. 45-49.

Swalla et al., "The Independence of Myogenesis and Chondrogenesis in Micromass Cultures of Chick Wing Buds," Developmental Biology, (1986), vol. 116, pp. 31-38.

Von Der Mark et al., "Relationship Between Cell Shape and Type of Collagen Synthesised as Chondrocytes Lose Their Cartilage Phenotype in Culture," Nature, (1977), vol. 267:5611, pp. 531-532.

West et al., "Fibronectin Alters the Phenotypic Properties of Cultured Chick Embryo Chondroblasts," Cell, (1979), vol. 17:3, pp. 491-501.

Yoo et al., "The Chondrogenic Potential of Human Bone-Marrow-Derived Mesenchymal Progenitor Cells," J Bone Joint Surg. Am., (1998), vol. 80:12, pp. 1745-1757.

Zuk et al., "Multilineage Cells from Human Adipose Tissue: Implications for Cell-Based Therapies," Tissue Engineering, (2001), 7, 2, 211.

* cited by examiner

ADIPOSE TISSUE-DERIVED ADULT STEM OR STROMAL CELLS FOR THE REPAIR OF ARTICULAR CARTILAGE FRACTURES AND USES THEREOF

CROSS REFERENCE TO RELATED APPLICATIONS

This Application is a continuation-in-part of U.S. application Ser. No. 10/125,106, filed Apr. 18, 2002, now U.S. Pat. No. 6,841,150, which is a continuation of U.S. application Ser. No. 09/573,989, filed May 17, 2000, now U.S. Pat. No. 6,429,013, which in turn claims priority under Title 35 U.S.C. §119(e) to U.S. Provisional Application No. 60/149,850, filed Aug. 19, 1999.

FIELD OF THE INVENTION

This invention provides methods and compositions for the use of adipose tissue derived adult stem or stromal cells in combination with biocompatible, resorbable and non-resorbable materials for the repair of articular cartilage fractures.

BACKGROUND OF THE INVENTION

Articular cartilage provides a smooth mechanical surface and cushion at skeletal sites subjected to repetitive friction and high weight-bearing loads. In humans, articular cartilage is a relatively thin (<2 mm thick), avascular and acellular tissue located at the proximal and distal ends of the axial skeletal bones. Consequently, articular cartilage has little capacity for self repair [McPherson J M, Tubo R. 2000 in Principles of Tissue Engineering, Second Edition edit Lanza RP, Langer R, Vacanti J. Academic Press, San Diego, p 697–709]. Articular cartilage fractures occur in patients who have fallen and have absorbed the force of the impact directly across a joint space (knee, hip, or elbow). Upon examination, orthopedists routinely discover that the articular cartilage has broken into multiple fragments that may or may not remain adherent to the underlying bone scaffold. Orthopedists have few available alternatives for the treatment of these defects; these include debridement, osteochondral grafting, and mechanical supports [McPherson J M, Tubo R. 2000 in Principles of Tissue Engineering, Second Edition edit Lanza RP, Langer R, Vacanti J. Academic Press, San Diego, p 697–709].

Traumatic injuries to joints in adults are typically the result of a compressive force across the articular surface. This can lead to irreversible damage to the cartilage accompanied by comminution and/or depression of articular fragments. Convex surfaces such as the tibial plateau, distal radius and acetabulum are most often affected. Once the major bone/cartilage fragments are re-approximated and stabilized with plates and screws, the orthopedist is still faced with an as yet unsolved challenge, the resurfacing of residual articular defects with healthy, viable cartilage.

What is needed are compositions and methods for the repair or replacement of articular cartilage fractures utilizing tissues and compositions that allow for the re-growth of damaged or missing cartilage.

Therefore an object of the invention is to provide methods and composition for the use of isolated adipose tissue-derived adult stem or stromal cells in the repair of articular cartilage fractures and defects.

SUMMARY OF THE INVENTION

The present invention provides cells, methods and composition based upon the use of isolated adipose tissue-derived adult stem or stromal cells for the repair of articular cartilage fractures.

One aspect of the present invention is an insolated adipose tissue-derived adult stem cell differentiated to express at least one characteristic of a chondrocyte and implanted into a host in combination with a viscous, biocompatible liquid material, wherein the host is in need of articular cartilage repair. The biocompatible liquid is capable of gelling at body temperature and is selected from the group consisting of alginate, collagen, fibrin, hyaline, or plasma.

In another aspect of the invention, an insolated adipose tissue-derived adult stromal cell differentiated to express at least one characteristic of a chondrocyte is combined with a malleable, three dimensional matrix capable of filling an irregular cartilage defect and then implanted into a host. The matrix is a material including, but not limited to, polyglycolic-polylactic acid, poly-glycolic acid, poly-lactic acid, or suture-like material.

Still another aspect of the invention includes a composition comprising an isolated adipose tissue-derived adult stem cell differentiated to express at least one characteristic of a chondrocyte and implanted into the host combined with a malleable, three dimensional matrix capable of filling an irregular cartilage defect and a solid phase, biocompatible material of sufficient structural integrity to serve as an anchor within the cancellous bone underlying the articular cartilage defect.

Yet another aspect of the invention is a method of treating an articular cartilage defect in a host comprising implanting an isolated adipose tissue-derived adult stromal cell differentiated to express at least one characteristic of a chondrocyte implanted into a host. The method can further include an isolated adipose tissue-derived adult stromal cell in combination with a viscous, biocompatible liquid material, wherein the biocompatible liquid is capable of gelling at body temperature. The biocompatible liquid can include, but is not limited to, alginate, collagen, fibrin, hyaline, or plasma.

Still yet another aspect of the invention is a method of treating an articular cartilage defect in a host comprising implanting an isolated adipose tissue-derived adult stem cell differentiated to express at least one characteristic of a chondrocyte in combination with a malleable, three dimensional matrix capable of filling an irregular cartilage defect. The matrix can include, but is not limited to, polyglycolic-polylactic acid, poly-glycolic acid, poly-lactic acid, or suture-like material.

Another aspect of the invention includes a method of treating an articular cartilage defect in a host comprising implanting a composition comprising an isolated adipose tissue-derived adult stem cell differentiated to express at least one characteristic of a chondrocyte, a malleable, three dimensional matrix capable of filling an irregular cartilage defect and a solid phase, biocompatible material of sufficient structural integrity to serve as an anchor within the cancellous bone underlying the articular cartilage defect.

In another aspect of the invention, the biocompatible material comprises an isolated adipose tissue-derived stem cell differentiated to express at least one characteristic of an osteoblast grown in a matrix in vitro prior to implantation.

Other objects and features of the invention will be more fully apparent from the following disclosure and appended claims.

DETAILED DESCRIPTION OF THE INVENTION

Figure 1:
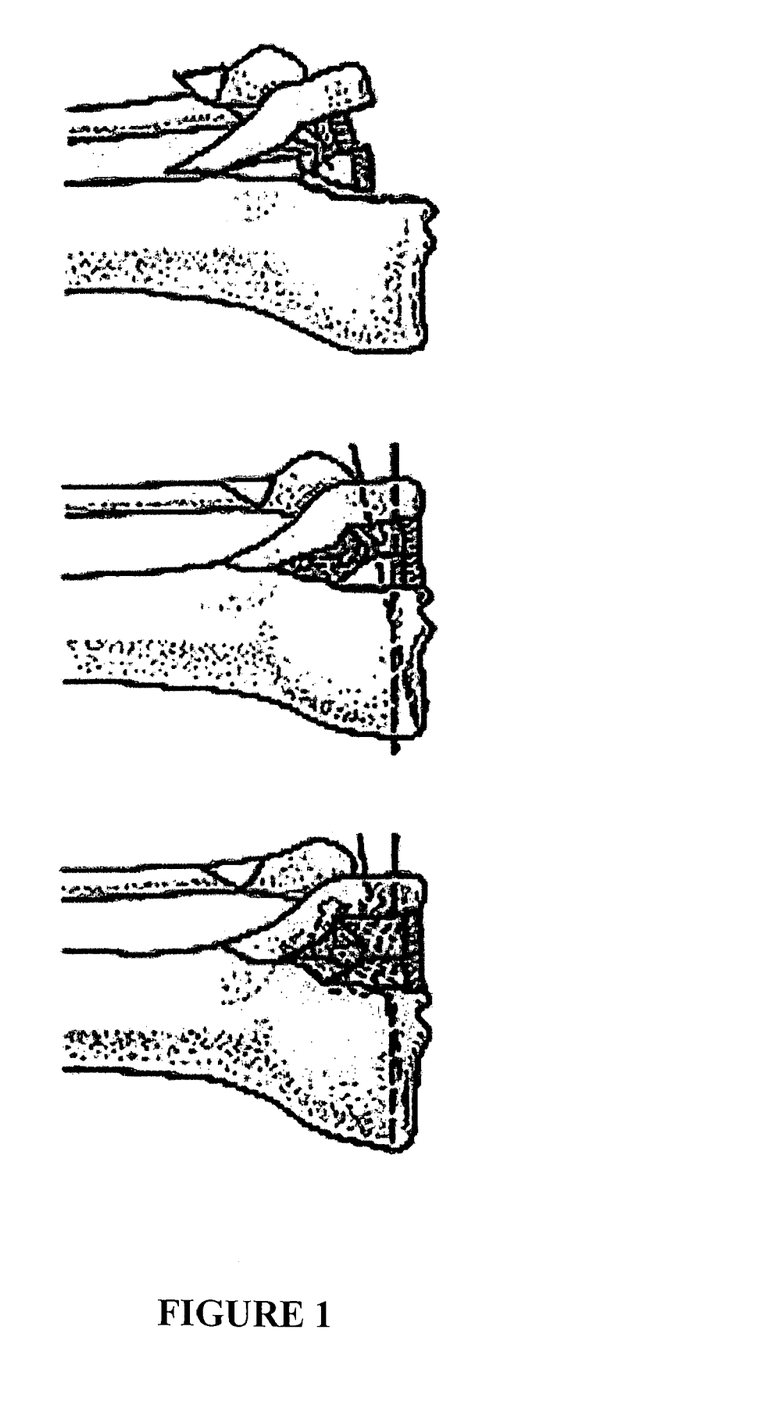
FIG. 1 is a schematic diagram of an articular cartilage defect depicting an implant of the current invention.
Figure 2:
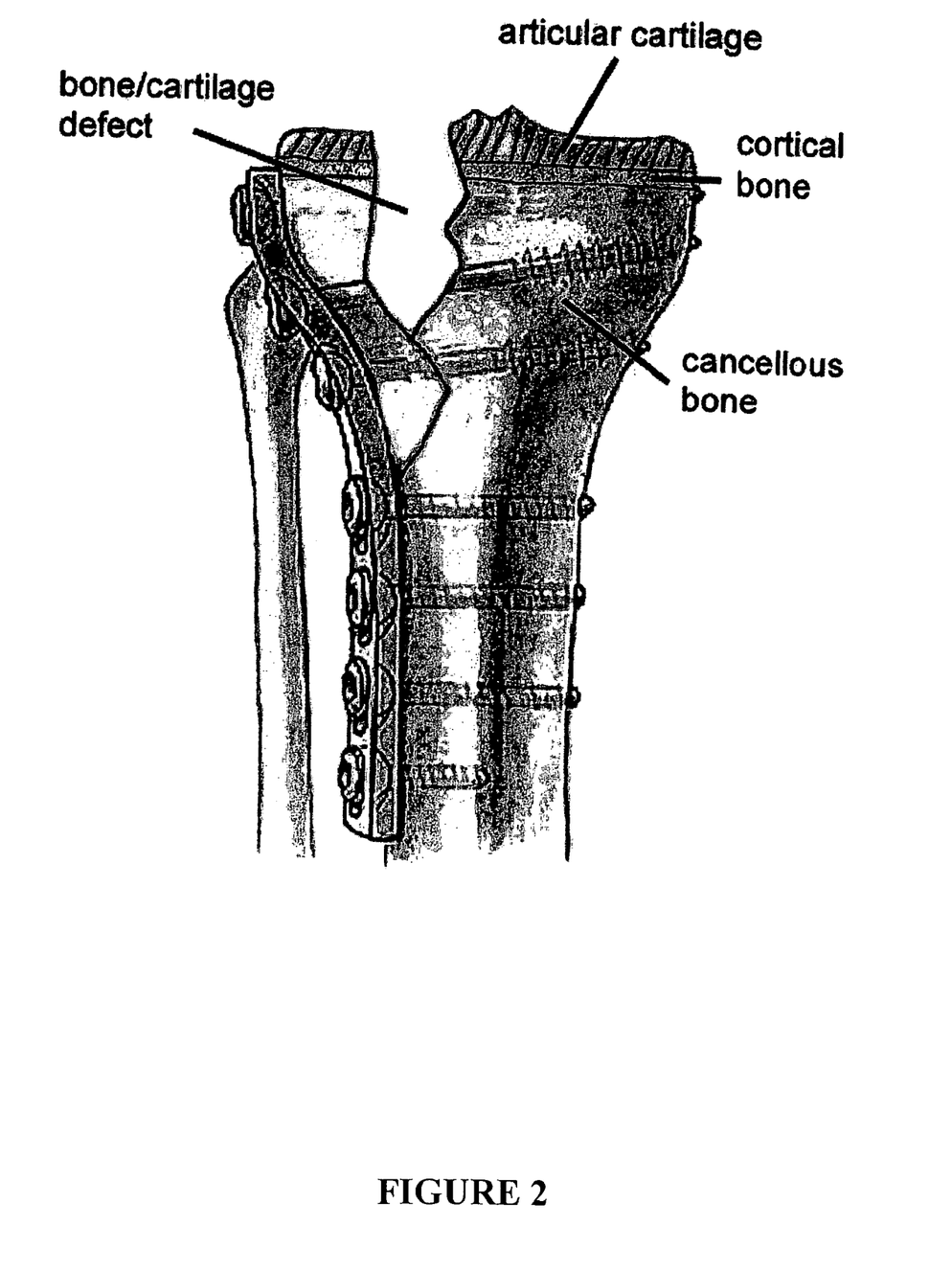
FIG. 2 is a schematic diagram of an articular cartilage defect along with a mechanical graft secured with screws into the joint region.
Figure 3:
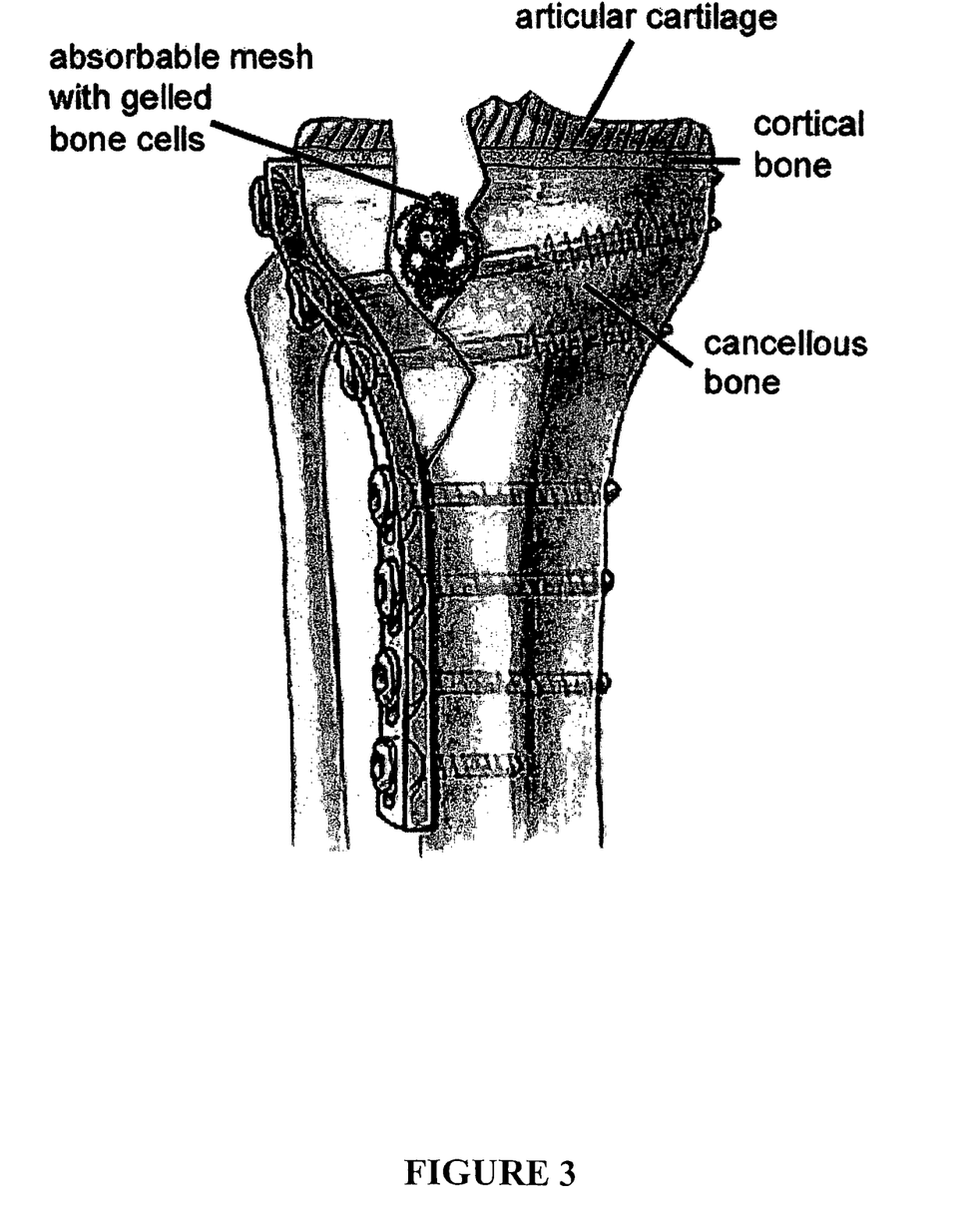
FIG. 3 is a schematic diagram of an articular cartilage defect along with a mechanical graft secured with screws into the joint region. The articular defect in need of repair is also depicted along with an absorbable mesh implant.
Figure 4:
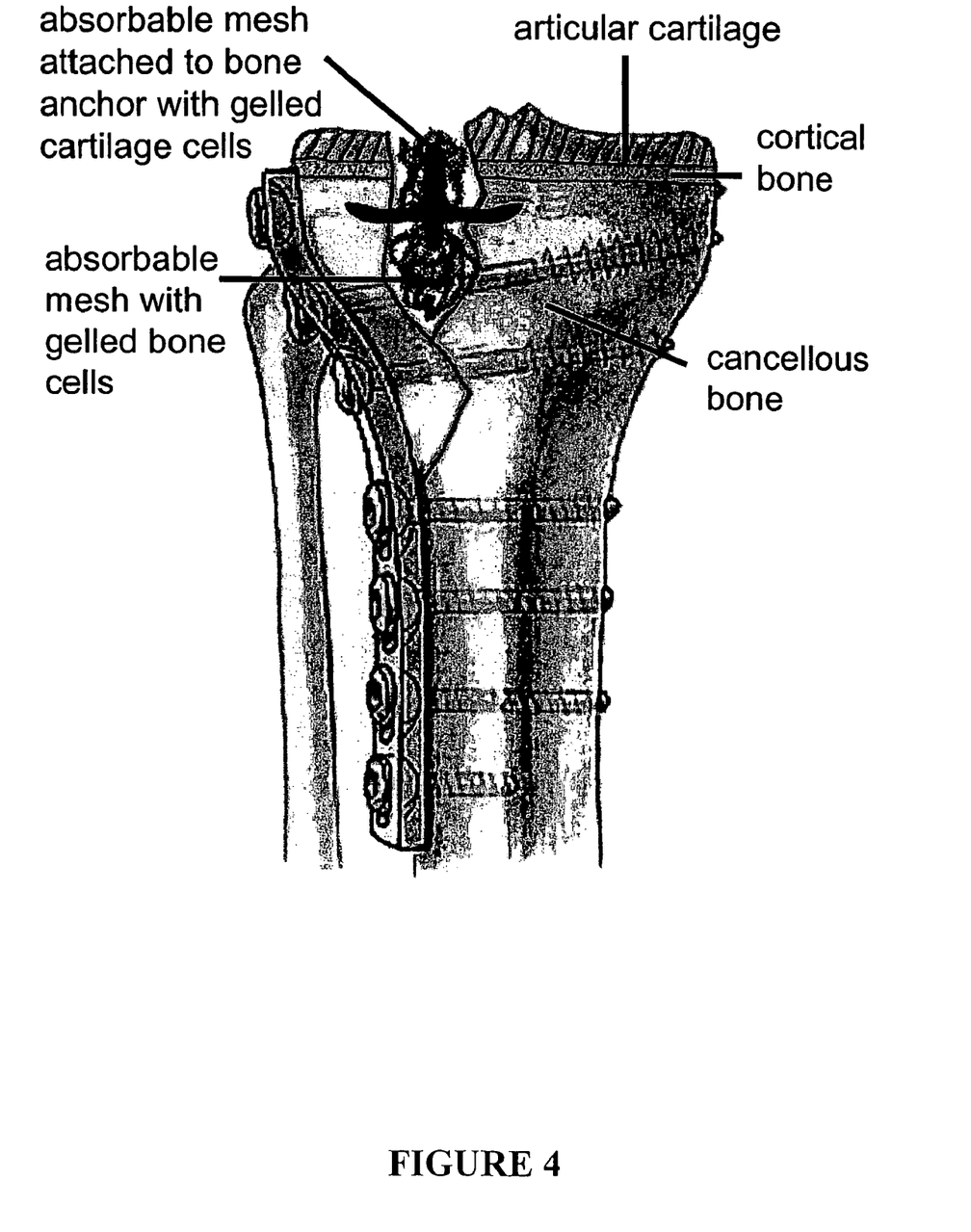
FIG. 4 is a schematic diagram of an articular cartilage defect along with a mechanical graft secured with screws into the joint region. The articular defect in need of repair is also depicted along with an absorbable mesh implant attached to a bone anchor with gelled cartilage cells and an absorbable mesh with gelled bone cells.

The present invention provides methods and composition for the use of isolated adipose tissue-derived adult stem or stromal cells for the repair of articular cartilage fractures. One aspect of the present invention is an isolated adipose tissue-derived adult stem cell differentiated to express at least one characteristic of a chondrocyte and implanted into host, wherein the host is in need to articular cartilage repair. The cell can be combined with a viscous, biocompatible liquid material. In another aspect of the invention, an isolated adipose tissue-derived adult stromal cell differentiated to express at least one characteristic of a chondrocyte is combined with a malleable, three dimensional matrix capable of filling an irregular cartilage defect and then implanted into a host. The matrix is a material including, but not limited to, polyglycolic-polylactic acid, poly-glycolic acid, poly-lactic acid, or suture-like material. Alternatively, the matrix includes an isolated adipose tissue-derived stromal or stem cell differentiated to a cell possessing at least one characteristic of an osteoblast.

I. Definitions

"Biocompatible material" refers to any organic or inorganic compound that can be safely and effectively introduced into a patient's body for tissue engineering purposes. These include, but are not limited to: 1) materials with organic, viscous and gelling properties, such as, but not limited to, alginate, collagen, fibrin, and hyaline. "Materials with organic and malleable properties" refers to materials that can be used to create a solid scaffold, including, but limited to, polyglycolic polylactic acid (PGLA) sutures (Vicryl™) or other woven suture-like material; solid materials of inorganic (metal, plastic or other biocompatible solid) or organic (bone allografts) properties suitable for insertion through a cartilage defect into the underlying cancellous bone to provide an anchor for sutures during an orthopedic procedure. The biocompatible material also includes a matrix comprising an isolated adipose tissue-derived stem cell differentiated to express at least one characteristic of an osteoblast.

"Chondrocytes" or "cartilage cells" refer to cells that are capable of expressing a characteristic biochemical marker of chondrocytes, including but not limited to collagen type II, chondroitin sulfate, keratin sulfate and characteristic morphologic markers, including but not limited to the rounded morphology observed in culture, and able to secrete collagen type II.

"Chondroinductive agent", "chondroinductive factor" or "chondroinductive substance" refer to any natural or synthetic, organic or inorganic chemical or biochemical compound, factor or combination of compounds or factors, or any mechanical or physical device, container, influence or force that can be applied to human adipose tissue-derived stromal cells so as to effect in vitro chondrogenic induction or the production of chondrocytes. The chondroinductive agent is selected individually or in combination from the groups consisting of i) a glucocorticoid such as dexamethasone; ii) a member of the transforming growth factor-beta (TGF-β) superfamily such as bone morphogenic protein (BMP: BMP-2,-4; TGF-β1,2,3; insulin-like growth factor (IGF); platelet derived growth factor (PDGF); epidermal growth factor (EGF); acidic fiborblastic growth factor; basic fibroblastic growth factor, hepatocytic growth factor, keratocytic growth factor, osteogenic proteins (OP-1,2,3); inhibin A or chondrogenic stimulating activity factor; iii) a component of the collagenous extracellular matrix such as collagen I; iv) a vitamin A analogue such as retinoic acid; and v) ascorbate or other vitamin C-related analogue.

"Non-peptide growth factors" refers to steroids, retinoids and other chemical compounds or agents that induce differentiation. These include, but are not limited to, 1,25 dihydroxyvitamin $D_3$, dexamethasone, hydrocortisone, retinoic acid, and 9-cis retinoic acid.

"Developmental phenotype" is the potential of a cell to acquire a particular physical phenotype through the process of differentiation.

"Genotype" is the expression at least one messenger RNA transcript of a gene associated with a differentiation pathway.

"Autoimmune disease" is intended to encompass any immune mediated process, humoral or cellular, that results in the rejection and destruction of the hosts' end organ. The etiology of this process can include, but is not limited to, an immune response to an infection by an agent such as a virus, an inborn metabolic propensity to autoimmune dysfunction, or a chemical exposure.

By "biomaterial matrices" is meant any biocompatible compound, resorbable or non-resorbable, which is able support the adherence, growth, differentiation, proliferation, vascularization, and three-dimensional modeling of adipose tissue-derived stem cells into a soft tissue or adipose tissue depot either in vivo or ex vivo. These include, but are not limited to, poly-lactic acid, poly-glycolic acid, hyaluronates, derivatives of glycosaminoglycans, alginate, collagen type I and its derivatives, collagen type IV and its derivatives, any other collagen type and its derivatives, or any combination thereof.

By "chemical inducing factors" is meant any chemical agent, either protein, lipid, or carbohydrate in character, which enhances the adherence, growth, differentiation, proliferation, vascularization and three-dimensional modeling of adipose tissue-derived stem or stromal cells into articular cartilage depot either in vivo or ex vivo. These include, but are not limited to, monobutyrin, thiazolidinediones, glucocorticoids, and long chain fatty acids.

By "protein growth factors and cytokines" is meant any protein hormone, growth factor, or cytokine which enhances the adherence, growth, differentiation, proliferation, vascularization, and three-dimensional modeling of adipose tissue-derived stem cells into articular cartilage depot either in vivo or ex vivo. These include but are not limited to, vascular endothelial growth factor, fibroblast growth factor (basic), bone morphogenetic protein 4, bone morphogenetic protein 7, insulin and its analogues, leptin, and growth hormone.

II. Adipose-Derived Stem or Stromal Cells

Adipose tissue offers a source of multipotential stromal cells. Adipose tissue is readily accessible and abundant in many individuals. Obesity is a condition of epidemic proportions in the United States, where over 50% of adults exceed the recommended BMI based on their weight and height. Adipocytes can be harvested by liposuction on an outpatient basis. This is a relatively non-invasive procedure with cosmetic effects that are acceptable to the vast majority of patients. It is well documented that adipocytes are a replenishable cell population. Even after surgical removal by liposuction or other procedures, it is common to see a recurrence of adipocytes in an individual over time. This suggests that adipose tissue contains stromal stem cells that are capable of self-renewal.

"Adipose stem or stromal cells" refers to multipotent stromal cells or stem cells that originate from adipose tissue and are capable of self-renewal. By "adipose" is meant any fat tissue. The adipose tissue may be brown or white adipose tissue, derived from subcutaneous, omental/visceral, mammary, gonadal, or other adipose tissue site. Preferably, the adipose is subcutaneous white adipose tissue. Such cells may comprise a primary cell culture or an immortalized cell line. The adipose tissue may be from any organism having fat tissue. Preferably, the adipose tissue is mammalian, most preferably the adipose tissue is human. These cells express a unique combination of cell surface proteins that can include, but are not limited to, the tetraspan protein CD9, CALLA (CD10), aminopeptidase N (CD13), integrin $\beta 1$ (CD29), hyaluronate receptor (CD44), integrin $\alpha$ 4 and 5 (CD49d, CD49e), ICAM-1 (CD54), decay accelerating factor (CD55), complement protectin (CD59), endoglin (CD105), VCAM-1 (CD106), Muc-1,8 (CD146), and ALCAM (CD166) [Gronthos, et al. J. Cell Physiol. 2001 October; 189(1):54–63].

There are currently methods available for the ordinary isolation, expansion, and differentiation of human adipose tissue-derived stem or stromal cells [Burris et al Mol Endocrinol 1999, 13:410–7; Erickson et al Biochemical & Biophysical Research Communications 2002, 290:763–9; Gronthos, et al. J Cell Physiol. 2001 October;189(1):54–63; Halvorsen, et al, Metabolism 2001, 50:407–413; Halvorsen, et al, Tissue Eng. 2001 December;7(6):729–41; Harp, et al. Biochem Biophys Res Commun 2001, 281:907–912; Saladin et al 1999, Cell Growth & Diff 10:43–48; Sen, et al. Journal of Cellular Biochemistry 2001, 81:312–319; Zhou et al Biotechnol Techniq 1999, 13:513–517]. Adipose tissue-derived stem cells are obtained from minced human adipose tissue by collagenase digestion and differential centrifugation according to known techniques [Halvorsen, et al, Metabolism 2001, 50:407–413; Hauner, et al, J Clin Invest 1989, 84:1663–1670; Rodbell, et al, J Biol Chem 1966, 241:130–139].

It has been demonstrated that human adipose tissue-derived stem cells can differentiate along the adipocyte, chondrocyte, and osteoblast lineage pathways [Erickson et al Biochemical & Biophysical Research Communications 2002, 290:763–9; Gronthos, et al. J Cell Physiol. 2001 October;189(1):54–63; Halvorsen, et al, Metabolism 2001, 50:407–413; Halvorsen, et al, Tissue Eng. 2001 December; 7(6):729–41; Harp, et al. Biochem Biophys Res Commun 2001, 281:907–912; Saladin et al 1999, Cell Growth & Diff 10:43–48; Sen, et al. Journal of Cellular Biochemistry 2001, 81:312–319; Zhou et al Biotechnol Techniq 1999, 13:513–517; Zuk, et al., Tissue Eng 2001, 7:211–28].

Adipose tissue offers many practical advantages for tissue engineering applications. First, it is abundant. Second, it is accessible to harvest methods with minimal risk to the patient. Third, it is replenishable. While stromal cells represent less than 0.01% of the bone marrow's nucleated cell population, there are up to $8.6 \times 10^4$ stem cells per gram of adipose tissue [Sen, et al. Journal of Cellular Biochemistry 2001, 81:312–319]. Ex vivo expansion over 2 to 4 weeks yields up to 500 million stem cells from 0.5 kilograms of adipose tissue. These cells can be used immediately or cryopreserved for future autologous or allogeneic applications.

WO 00/53795 to the University of Pittsburgh and The Regents of the University of California and US Patent Application No. 2002/0076400 assigned to the University of Pittsburgh, disclose adipose-derived stem cells and lattices substantially free of adipocytes and red blood cells and clonal populations of connective tissue stem cells. The cells can be employed, alone or within biologically-compatible compositions, to generate differentiated tissues and structures, both in vivo and in vitro. Additionally, the cells can be expanded and cultured to produce hormones and to provide conditioned culture media for supporting the growth and expansion of other cell populations. In another aspect, these publications disclose a lipo-derived lattice substantially devoid of cells, which includes extracellular matrix material form adipose tissue. The lattice can be used as a substrate to facilitate the growth and differentiation of cells, whether in vivo or in vitro, into anlagen or mature tissue or structures.

U.S. Pat. No. 6,391,297 assigned to Artecel Sciences discloses a composition of an isolated human adipose tissue-derived stromal cell that has been differentiated to exhibit at least one characteristic of an osteoblast that can be used in vivo to repair bone and treat bone diseases. This adipose-derived osteoblast-like cell can be optionally genetically modified or combined with a matrix.

U.S. Pat. No. 6,426,222 assigned to BioHoldings International discloses methods for inducing osteoblast differentiation from human extramedullary adipose tissue by incubating the adipose tissue cells in a liquid nutrient medium that must contain a glucocorticoid.

WO 00/44882 and U.S. Pat. No. 6,153,432 listing Halvorsen et al as inventors, discloses methods and compositions for the differentiation of human preadipocytes isolated from adipose tissue into adipocytes bearing biochemical, genetic, and physiological characteristics similar to that observed in isolated primary adipocytes.

WO 01/62901 and published U.S. Patent Application No. 2001/0033834 to Artecel Sciences discloses isolated adipose tissue-derived stromal cells that have been induced to express at least one phenotypic characteristic of a neuronal, astroglial, hematopoietic progenitor or hepatic cell. In addition an isolated adipose tissue-derived stromal cell that has been dedifferentiated such that there is an absence of adipocyte phenotypic markers is also disclosed.

U.S. Pat. No. 6,429,013 assigned to Artecel Sciences discloses compositions directed to an isolated adipose tissue-derived stromal cell that has been induced to express at lease one characteristic of a chondrocyte. Methods are also disclosed for differentiating these cells.

U.S. Pat. No. 6,200,606 to Peterson et al. discloses that precursor cells which have the potential to generate bone or cartilage can be isolated from a variety of hematopoietic and non-hematopoietic tissues including peripheral blood, bone marrow and adipose tissue.

Zilberfarb et al. (J. Cell Science 110, 801–807, 1997), "Human Immortalized Brown Adipocytes Express Functional $\beta_3$-Adrenoreceptor Coupled to Lipolysis" discloses an immortalized cell line of human brown pre-adipocytes differentiated in culture into adipocytes that express the $\beta_3$-adrenoreceptor functionally coupled to adenylate cyclase and lipolysis.

Adipose tissue from a variety of sources may be processed to produce stem cells for the generation of a cell possessing at least one genotypic or phenotypic characteristic of a chondrocyte for repair of an articular cartilage defect. In a preferred method, adipose tissue is isolated from a mammalian subject, preferably a human subject. The adipose tissue may be from subcutaneous, breast or perirenal sites. Preferably the adipose tissue is subcutaneous. Liposuction surgery or penniculectomy may provide subcutaneous adipose tissue.

The adipose tissue derived stromal cells useful in the invention are isolated by a variety of methods known to those skilled in the art including but not limited to those described in WO 00/53795 to the University of Pittsburgh et al. Preferably the stem cells are isolated from the stromal vascular fraction by the method of Rodbell (1974).

As a non-limiting example, in one method of isolating adipose tissue derived stromal cells, the adipose tissue is treated with collagenase at concentrations between 0.01 to 0.5%, preferably 0.04 to 0.2%, most preferably 0.1%, at temperatures between 25° to 50° C., preferably between 33° to 40° C., most preferably at 37° C., for periods of between 10 minutes to 3 hours, preferably between 30 minutes to 1 hour, most preferably 45 minutes. The cells are then subjected to differential centrifugation directly in media or over a Ficoll or Percoll or other particulate gradient. Cells are centrifuged at speeds of between 100 to 3000×g, more preferably 200 to 1500×g, most preferably at 500×g for periods of between 1 minute to 1 hour, more preferably 2 to 15 minutes, most preferably 5 minutes, at temperatures of between 4° to 50° C., preferably between 20° to 40° C., most preferably at 25° C.

In yet another method of isolating adipose-derived stromal cells a mechanical system such as described in U.S. Pat. No. 5,786,207 to Katz et al is used. A system is employed for introducing an adipose tissue sample into an automated device, subjecting it to a washing phase and a dissociating phase wherein the tissue is agitated and rotated such that the resulting cell suspension is collected into a centrifuge-ready receptacle. In such a way, the adipose-derived cells are isolated from a tissue sample, preserving the cellular integrity of the desired cells.

III. Inducement of Adipose-Derived Stromal Cells To Exhibit At Least One Characteristic of a Chondrocyte to Be Used in the Repair of An Articular Cartilage Defect The invention includes compositions comprising an adipose tissue derived stromal cell induced to form a cell that expresses at least one genotypic or phenotypic characteristic of a chondrocyte. Non-limiting examples of how to induce the differentiation of adipose-derived stromal cells include: 1) the use of cell media; 2) the use of support cells; 3) direct implantation of the undifferentiated cells into the tissue of a patient; and 4) cellular engineering techniques.

A) Cell Media Inducement

Treatment of the adipose-derived stromal cells with a medium containing a combination of serum, embryonic extracts, purified or recombinant growth factors, cytokines, hormones, and/or chemical agents, in a 2-dimensional or 3-dimensional microenvironment, will induce differentiation.

One non-limiting example of a method for differentiating an adipose-derived cells into a cell having a genotypic or phenotypic property of a chondrocyte, comprises: plating isolated adipose-derived adult stem cells at a desired density, including but not limited to a density of about 1,000 to about 500,000 cells/cm$^2$; incubating the cells in a chemically defined culture medium comprising at least one compound selected from the group consisting of: growth factor, hormone, cytokine, serum factor, nuclear hormone receptor agonist, or any other defined chemical agent.

More specifically, the medium for differentiating adipose tissue-derived stem cells into a chondrocyte (hereinafter referred to as the "differentiation medium") comprises a defined cell culture medium having or supplemented with 1000–4500 mg/liter glucose; a biological buffer; 0–100 µM biotin; 0–100 µM pantothenate; about 0.1 to 5 mM isobutylmethylxanthine; 10–1000 nM human insulin or an equivalent amount of an insulin analogue; about 10% to 0% fetal bovine serum; 10 nM to 1 µM of a glucocorticoid; and a concentration of a chondroinductive agent effective to stimulate differentiation of human stem cells, between 10 nM to 100 micromolar.

By a "defined cell culture medium" is meant a serum free, chemically defined cell growth medium. It is critical that the medium contains biotin and pantothenate. Preferably the medium is Dulbecco's Modified Eagle Medium, Ham's F-12 Nutrient Broth (1:1 v/v) or Earl's medium. However, a variety of media, known to those skilled in the art, are useful in the methods of the invention.

Additional compounds may be included or added to the medium. For example, antibiotics, such as penicillin, streptomycin and fungizone are useful additives to the media of the invention.

The pH of the medium must be maintained during use, either through the inclusion of a biological buffer or by adjusting the CO$_2$ content in the atmosphere of the incubator. Preferably the medium is buffered by about 15 mM NaHCO$_3$ and about 15 mM HEPES pH 7.4 to a physiological pH.

Fetal bovine serum (FBS) is added to the defined cell culture medium at a concentration of about 10 to 20%.

The methods of the invention utilize the above media to achieve at least 50–95% differentiation of cultured human stem cells into chondrocytes. Thus, it is a further object of the invention to provide methods for differentiating human stem cells into chondrocytes, comprising:

a) plating isolated human cells at a density of about 25,000 to 120,000 cells/cm$^2$ in a medium comprising a defined cell culture medium having or supplemented with 1000–4500 mg/liter glucose; a biological buffer; and about 10% to 0% fetal bovine serum (vol/vol);

b) incubating said cells at about 37° C. in about 5% CO$_2$ for 4–24 hours until said cells are about 95–100% confluent;

c) replacing said medium with a differentiation medium comprising a defined cell culture medium having or supplemented with 1000–4500 mg/liter glucose; 0–100 µM biotin, 0–100 µM pantothenate, a biological buffer; about 0.1 to 0.5 mM isobutylmethylxanthine; 10 nM to 1 µM human insulin; about 10% to 0% fetal bovine serum; 16 nM to 1 µM of a glucocorticoid; and a concentration of a chondroinductive agent effective to stimulate differentiation of a human stem cells;

d) incubating said cells at about 37° C. in about 5% CO$_2$ for 3 days;

e) replacing said differentiation medium with an adipocyte medium comprising a cell culture medium having or supplemented with 1000–4500 mg/liter glucose; 0–100 µM biotin, 0–100 µM pantothenate, a biological buffer; 10 nM to 1 µM human insulin; about 10% to 0% fetal bovine serum; 16 nM to 1 µM of a glucocorticoid;

f) incubating said cells at about 37° C. in about 5% $CO_2$ for about 7–20 days and refeeding said cells with said adipocyte medium every 3–4 days.

When initially plating stem cells in medium (step a), the cells must be plated at a density of 25,000–120,000 cells/cm$^2$. Preferably the cell density is greater than 30,000 cells/cm$^2$. Lower density plating of stem cells results in an overall lower differentiation percentage. When plated at a density of greater than 25,000 cells/cm$^2$ the stem cells are usually confluent after overnight incubation. If cells are not fully confluent at this point, they may be incubated for up to another 24 hours prior to refeeding with differentiation medium. Longer incubations prior to re-feeding result in a lower differentiation percentage.

Once the cells have been exposed to differentiation media (step c), they are susceptible to detaching: from the plate if the media is either completely removed or quickly added.

The disclosed methods offer the distinct advantage of culturing the cells in a single cultureware flask or container. Thus, the need for multiple cell passages and trypsin digestion to suspend the cells is completely eliminated, increasing both yield and quality of cells produced. A single cultureware flask or container also allows for longer growth periods, which facilitates the production of extracellular matrix proteins.

A variety of methods known to those skilled in the art may be used to determine the percentage of differentiated cells in vivo and ex vivo. Examples of such methods include those that assess biochemical or morphological characteristics, such as lipid deposits and chondrocyte-specific proteins or mRNAs.

Media useful in the methods of the invention contain fetal serum of bovine or other species origin at a concentration of at least 1–10%. Embryonic extract of chicken or other species origin is present at a concentration of about 1% to 30%, preferably at least about 5% to 15%, most preferably about 10%.

Additional components are optionally added to the culture medium. Such components include but are not limited to antibiotics, albumin, amino acids, and other components known to the art for the culture of cells. Additionally, components optionally are added to enhance the differentiation process.

B) Use of Support Cells To Promote the Differentiation of the Adipose-Derived Stromal Cells In another embodiment of the invention, support cells are used to promote the differentiation of the adipose-derived stromal cells prior to or following implantation into an animal host. The support cells can be human or non-human-animal derived cells. If non-human-animal support cells are used, the resulting differentiated cells are implanted via xenotransplantation.

Adipose-derived cells are isolated and cultured within a population of cells; most preferably the population is a defined population. The population of cells is heterogeneous and includes support cells for supplying factors to the cells of the invention. Support cells include other cell types which will promote the differentiation, growth and maintenance of the desired cells. As a non-limiting example, an adipose-derived stromal or stem cell that expresses at least one genotypic or phenotypic characteristic of a chondrocyte is first isolated by any of the means described above, and grown in culture in the presence of other support cells. For example, these support cells preferably possess the characteristic of adipose stromal cell types. In another embodiment, the support cells are derived from primary cultures of these cell types taken from cultured human organ tissue. In yet another embodiment, the support cells are derived from immortalized cell lines. In some embodiments, the support cells are obtained autologously. In other embodiments, the support cells are obtained allogeneically.

Support cells can also be genetically engineered to be support cells. The cells are genetically modified to express exogenous genes or to repress the expression of endogenous genes by any method described below or know to those skilled in the art.

C) Implantation

Adipose-derived stromal cells and differentiated cells expressing at least one genotypic or phenotypic characteristic of a chondrocyte that are useful in autologous and allogeneic transplantations are implanted into an animal. The differentiation takes place in vivo by means of factors found naturally in the environment or introduced factors along with the cellular implant. In one embodiment, the site of transplantation is a joint in need of articular cartilage repair. In other embodiments the site of transplantation is a joint in need of articular cartilage replacement. Preferably, the subject is mammalian, more preferably, the subject is human. The cell of the invention can be induced to differentiate in vitro or after implantation into a patient.

It is contemplated that when undifferentiated adipose-derived stromal cells are introduced into the subject, in one particular embodiment, they are introduced directly into a diseased joint in need of chondrocytes with or without any additional growth or differentiation factors. In yet another aspect of the invention, the undifferentiated adipose-derived stromal cells are introduced along with any of the support cells as described herein that will provide an environment suitable for the in vivo differentiation of the stromal cells. In another embodiment, the support cells are derived from primary cultures of these cell types. In yet another embodiment, the support cells are derived from immortalized cell lines. In some embodiments, the support cells are obtained autologously. In other embodiments, the support cells are obtained allogeneically.

In another embodiment, a dedifferentiated adipose-derived cell is provided in combination with a pharmaceutically acceptable carrier for a therapeutic application to an animal, including but not limited to tissue repair, regeneration, reconstruction or enhancement. Adipose-derived cells are cultured by methods such as disclosed in U.S. Pat. No. 6,153,432 to dedifferentiate the cells such that the dedifferentiated adult stem cells can then be induced to express genotypic or phenotypic characteristics of a chondrocyte. The dedifferentiated adipose-derived cells are modified to include a non-endogenous gene sequence for production of a desired extracellular matrix protein or peptide. The dedifferentiated adipose-derived cell can, in an alternative embodiment, be administered to a host in a two- or three-dimensional matrix for a desired therapeutic purpose. In one embodiment, the dedifferentiated cell is obtained autologously from the patient's own cells. Alternatively, the dedifferentiated cell is obtained allogeneically.

D) Genetic Manipulation of the Adipose-Derived Cells of the Invention

In yet another embodiment, the adipose-tissue derived cell expressing at least one genotypic or phenotypic characteristic of a chondrocyte is genetically modified to express exogenous genes or to repress the expression of endogenous genes and implanted into an animal. The invention provides a method of genetically modifying such cells and populations prior to implantation.

A nucleic acid construct comprising a promoter and the sequence of interest can be introduced into a recipient prokaryotic or eukaryotic cell either as a non-replicating DNA (or RNA) molecule, which can either be a linear molecule or, more preferably, a closed covalent circular molecule. Since such molecules are incapable of autonomous replication without an origin of replication, the expression of the gene can occur through the transient expression of the introduced-sequence. Alternatively, permanent expression can occur through the integration of the introduced DNA sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the desired nucleic acid sequence. The marker, if desired, can provide for prototrophy to an auxotrophic host, biocide resistance, e.g., resistance to antibiotics, or heavy metals, such as copper, or the like. The selectable marker gene sequence can either be directly linked to the DNA gene sequences to be expressed, or introduced into the same cell by co-transfection. Preferably, expression of the marker can be quantified.

In a preferred embodiment, the introduced nucleic acid molecule will be incorporated into a plasmid or viral vector capable of autonomous replication in the recipient host. Any of a wide variety of vectors can be employed for this purpose. Factors of importance in selecting a particular plasmid or viral vector include: 1) the ease with which recipient cells that contain the vector can be recognized and selected from those recipient cells which do not contain the vector; 2) the number of copies of the vector which are desired in a particular host; and 3) whether it is desirable to be able to "shuttle" the vector between host cells of different species.

Preferred eukaryotic vectors include for example, vaccinia virus, SV40, retroviruses, adenoviruses, adeno-associated viruses and a variety of commercially available, plasmid-based mammalian expression vectors that are familiar to those experienced in the art.

Once the vector or nucleic acid molecule containing the construct(s) has been prepared for expression, the DNA construct(s) can be introduced into an appropriate host cell by any of a variety of suitable means, i.e., transformation, transfection, viral infection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of the heterologous protein.

Introduced DNA being "maintained" in cells should be understood as the introduced DNA continuing to be present in essentially all of the cells in question as they continue to grow and proliferate. That is, the introduced DNA is not diluted out of the majority of the cells over multiple rounds of cell division. Rather, it replicates during cell proliferation and at least one copy of the introduced DNA remains in almost every daughter cell. Introduced DNA may be maintained in cells in either of two fashions. First, it may integrate directly into the cell's genome. This occurs at a rather low frequency. Second, it may exist as an extrachromosomal element, or episome. In order for an episome not to be diluted out during cell proliferation, a selectable marker gene can be included in the introduced DNA and the cells grown under conditions where expression of the marker gene is required. Even in the case where the introduced DNA has integrated in the genome, a selectable marker gene may be included to prevent excision of the DNA from the chromosome.

The genetically altered cells can then be introduced into an organism by a variety of methods under conditions for the transgene to be expressed in vivo. As a non-limiting example, the transgene can encode for the production of an extracellular matrix protein, preferably wherein the transgene encodes for the production of collagen. The cells containing the transgene for the extracellular matrix protein can then be introduced into the animal. Alternatively, the cells containing the transgene are injected intraperitoneally or into some other suitable organ depot site.

E) Cellular Characterization

Characterization of the resulting differentiated cells involves the identification of surface and intracellular proteins, genes, and/or other markers indicative of the lineage commitment of the stromal cells to a particular differentiated state. These methods can include, but are not limited to, (a) detection of cell surface proteins by immunofluorescent methods using protein specific monoclonal antibodies linked using a secondary fluorescent tag, including the use of flow cytometric methods; (b) detection of intracellular proteins by immunofluorescent methods using protein specific monoclonal antibodies linked using a secondary fluorescent tag, including the use of flow cytometric methods; (c) detection of cellular gene expression by polymerase chain reaction, in situ hybridization, and/or northern blot analysis.

Adipocyte differentiated cells may be characterized by the identification of surface and intracellular proteins, genes, and/or other markers indicative of the lineage commitment of the stromal cells to a particular differentiated state. These methods, which are described above, include, but are not limited to, (a) detection of cell surface proteins by immunofluorescent assays such as flow cytometry or in situ immunostaining of adipose-derived stromal cells surface proteins such as CD36, lipoprotein lipase, and pref-1 in addition to those outlined in Gronthos et al 2001 (b) detection of intracellular proteins by immunofluorescent methods such as flow cytometry or in situ immunostaining of adipose tissue-derived stromal cells using specific monoclonal antibodies; (c) detection of the expression of chondrocyte lineage selective mRNAs by methods such as polymerase chain reaction, in situ hybridization, and/or other blot analysis (See Gimble et al. 1989 Blood 74:303–311).

F) Use of the Cells of the Invention as Therapeutic Agents

The adipose-derived cells and populations described herein can be employed as therapeutic agents in animals, for example, in the repair or replacement of articular cartilage. Generally, such methods involve transferring the cells to the desired depot. The cells are transferred to the desired tissue by any method appropriate, which generally vary according to the tissue type. For example, cells can be transferred to a graft by bathing the graft or infusing it with culture medium containing the cells. Alternatively, the cells can be seeded on the desired site within the tissue to establish a population. Cells can be transferred to sites in vivo using devices well know to those skilled in the art for example, catheters, trocars, cannulae, or stents seeded with the cells.

G) Biocompatible Materials

Biomaterial science is an established and evolving field [Takayama et al, Principles of Tissue Engineering, Second Edition edit Lanza RP, Langer R, Vacanti J. Academic Press, San Diego, 2000, pg 209–218; Saltmann, et al, Principles, of Tissue Engineering, Second Edition edit Lanza RP., Langer R, Vacanti J. Academic Press, San Diego, 2000, p 221–236; Hubbell, et al, Principles of Tissue Engineering, Second Edition edit Lanza R P, Langer R, Vacanti J. Academic Press, San Diego, 2000, p 237–250; Thomson, et al, Principles of Tissue Engineering, Second Edition edit Lanza RP, Langer R. Vacanti J. Academic Press, San Diego, 2000, p 251–262; Pachence, et al, Principles of Tissue Engineering, Second Edition edit Lanza RP, Langer R, Vacanti J. Academic Press, San Diego, 2000, p 263–278]. Chemists have developed methods to synthesize polymers to direct and modulate cell growth in vitro and in vivo. The physical properties of the polymers can be modulated to create solid and liquid matrices of specific strengths and viscosities. Some polymers are stable in vivo and will remain in a patient's body for up to years. Other polymers are biodegradable, resorbing at a fixed rate over time to allow replacement by newly synthesized extracellular matrix proteins. Resorption can occur within days to weeks or months following implantation [Pachence, et al, Principles of Tissue Engineering, Second Edition edit Lanza RP, Langer R. Vacanti J. Academic Press, San Diego, 2000, p 263–278].

The cells of the present invention can be combined with a viscous, biocompatible liquid material. The biocompatible liquid is capable of gelling at body temperature and is selected from the group consisting of alginate, collagen, fibrin, hyaline, or plasma. The cells can also be combined with a malleable, three dimensional matrix capable of filling an irregular cartilage defect. The matrix is a material including, but not limited to, polyglycolic-polylactic acid, polyglycolic acid, poly-lactic acid, or suture-like material.

The invention also includes an articular cartilage repairing composition comprising an isolated adipose tissue-derived adult stem cell differentiated to express at least one characteristic of a chondrocyte and implanted into host, in combination with a malleable, three dimensional matrix capable of filling an irregular cartilage defect and a solid phase, biocompatible material of sufficient structural integrity to serve as an anchor within the cancellous bone underlying the articular cartilage defect.

A method of treating an articular cartilage defect in a host comprising implanting an isolated adipose tissue-derived adult stem cell differentiated to express at least one characteristic of a chondrocyte in combination with a viscous, biocompatible liquid material, wherein the biocompatible liquid is capable of gelling at body temperature is also provided. The biocompatible liquid can include, but is not limited to alginate, collagen, fibrin, hyaline, or plasma.

The invention also comprises a method of treating an articular cartilage defect in a host comprising implanting an isolated adipose tissue-derived adult stem cell differentiated to express at least one characteristic of a chondrocyte in combination with a malleable, three dimensional matrix capable of filling an irregular cartilage defect. The matrix can include, but is not limited to, polyglycolic-polylactic acid, poly-glycolic acid, poly-lactic acid, or suture-like material.

Another method is included for treating an articular cartilage defect in a host comprising implanting a composition comprising an insolated adipose tissue-derived adult stem or stromal cell differentiated to express at least one characteristic of a chondrocyte, a malleable, three dimensional matrix capable of filling an irregular cartilage defect and a solid phase, biocompatible material of sufficient structural integrity to serve as an anchor within the cancellous bone underlying the articular cartilage defect. In one embodiment of the invention, the method includes a biocompatible material which includes an adipose tissue-derived cell differentiated to possess at least one characteristic of an osteoblast. This cell can be isolated and differentiated by any of the methods disclosed herein.

IV. Tissue Engineering

Adipose-derived cells can be isolated and differentiated into a cell that possesses at least one characteristic of a chondrocyte and then engineered into tissue matter, tissues or organs to be implanted into an animals. The tissue matter can include, for example a portion of, or even a whole joint. As such, prior to implantation into an animal, the cells described herein are used in combination with any known technique of tissue engineering, including but not limited to those technologies described in the following: U.S. Pat. Nos. 5,902,741 and 5,863,531 to Advanced Tissue Sciences, Inc.; U.S. Pat. No. 6,139,574, Vacanti et al.; U.S. Pat. No. 5,759,830, Vacanti et al.; U.S. Pat. No. 5,741,685, Vacanti,; U.S. Pat. No. 5,736,372, Vacanti et al.; U.S. Pat. No. 5,804,178, Vacanti et al.; U.S. Pat. No. 5,770,417, Vacanti et al.; U.S. Pat. No. 5,770,193, Vacanti et al.; U.S. Pat. No. 5,709,854, Griffith-Cima et al.; U.S. Pat. No. 5,516,532, Atala et al.; U.S. Pat. No. 5,855,610, Vacanti et al.; U.S. Pat. No. 5,041,138, Vacanti et al.; U.S. Pat. No. 6,027,744, Vacanti et al.; U.S. Pat. No. 6,123,727, Vacanti et al.; U.S. Pat. No. 5,536,656, Kemp et al.; U.S. Pat. No. 5,144,016, Skjak-Braek et al.; U.S. Pat. No. 5,944,754, Vacanti; U.S. Pat. No. 5,723,331, Tubo et al.; and U.S. Pat. No. 6,143,501, Sittinger et al.

To produce such a structure, the cells and populations are maintained under conditions suitable for them to expand and divide to form the joint. This may be accomplished by transferring them to an animal typically at a site where the new matter is desired. Thus, the invention can facilitate the regeneration of tissue within an animal where the cells are implanted into such tissues.

In still other embodiments, the cells are induced to differentiate and expand into tissue in vitro prior to implantation into an animal. As such, the cells are cultured on substrates that facilitate formation into three-dimensional structures conducive for tissue development. Thus, for example, the cells are cultured or seeded onto a bio-compatible lattice, such as one that includes extracellular matrix material, synthetic polymers, cytokines, growth factors, etc. Such a lattice can be molded into desired shapes for facilitating the development of tissue types. The lattice can be formed from polymeric material, having fibers as a mesh or sponge. Such a structure provides sufficient area on which the cells can grow and proliferate. Desirably, the lattice is biodegradable over time, so that it will be absorbed into the animal matter as it develops. Suitable polymers can be formed from monomers such as glycolic acid, lactic acid, propyl fumarate, caprolactone, and the like. Other polymeric material can include a protein, polysaccharide, polyhydroxy acid, polyorthoester, polyanhydride, polyphosphozene, or a synthetic polymer, particularly a biodegradable polymer, or any combination thereof. Also, the lattice can include hormones, such as growth factors, cytokines, morphogens (e.g. retinoic acid etc), desired extracellular matrix materials (e.g. fibronectin, laminin, collagen etc) or other materials (e.g. DNA, viruses, other cell types etc) as desired.

The cells are introduced into the lattice such that they permeate into interstitial spaces therein. For example, the matrix can be soaked into a solution or suspension containing the cells, or they can be infused or injected in the matrix.

Preferably, a hydrogel formed by cross-linking of a suspension including the polymer and also having the inventive cells dispersed therein is used. This method of formation permits the cells to be dispersed throughout the lattice, facilitating more even permeation of the lattice with the cells. Of course, the composition also can include support cells for supplying factors to the cells of the invention. Support cells include other cell types which will promote the differentiation, growth and maintenance of the adipocyte cells.

Those skilled in the art will appreciate that lattices suitable for inclusion into the implanted material can be derived from any suitable source, e.g. Matrigel™, and can of course include commercial sources for suitable lattices. Another suitable lattice can be derived from the acellular portion of adipose tissue for example adipose tissue extracellular matrix substantially devoid of cells. Typically such adipose-derived lattices include proteins such as proteoglycans, glycoproteins, hyaluronin, fibronectins, collagens and the like, all of which serve a excellent substrates for cell growth. Additionally, such adipose-derived lattices can include hormones, cytokine, growth factors and the like. Those skilled in the art would be aware of methods for isolating such an adipose-derived lattice such as that disclosed in WO 00/53795 to the University of Pittsburgh.

In yet another embodiment of the invention, tissue is created using solid free-form fabrication methods to allow for tissue regeneration and growth for implantation into an animal. Such techniques are disclosed, for example, in U.S. Pat. No. 6,138,573 to Vacanti et al and allow the creation of a partial or whole joint for implantation into a human in need thereof. Creation of such partial or whole joints is accomplished with the cells of the present invention obtained in an autologous manner. Alternatively, such partial or whole joints are created from cells of the invention that were obtained in an allogeneic manner. It is contemplated that any method known to those skilled in the art is useful for engineering tissue from the cells of the invention. As a non-limiting example, U.S. Pat. No. 6,022,743 and 5,516,681 to Naughton et al (Advanced Tissue Sciences) disclose methods for 3-dimensional cell culture systems such engineering.

Such techniques could easily be adapted for other types of tissue repair, for example, the construction and repair of a joint in need of articular cartilage repair. These techniques involve the seeding and implanting of cells onto a matrix to form tissue, and structural components which can additionally provide controlled release of bioactive agents. The matrix is characterized by a network of lumens functionally equivalents to the naturally occurring vasculature of the tissue formed by the implanted cells and which is further lined with endothelial cells. The matrix is further coupled to blood vessels or other ducts at the time of implantation to form a vascular or ductile network throughout the matrix. The free-form fabrication techniques refer to any technique know in the art that builds a complex 3-dimensional object as a series of 2-dimensional layers. The methods can be adapted for use with a variety of polymeric, inorganic and composite materials to create structures with defined compositions, strengths and densities. Thus, utilizing such methods, precise channels and pores can be created within the matrix to control subsequent cell growth and proliferation within the matrix of one or more cells types having a defined function. In such a way, differentiated adipose-derived cells, corresponding to the various types of a particular organ's cells can be combined to form a partial or whole joint. Such cells are combined in the matrix to provide a vascular network lined with endothelial cells interspersed throughout the cells.

The cells, populations, lattices and compositions used in the methods of the invention are used in tissue engineering and regeneration in animals. Thus, the invention pertains to the use of an implantable structure incorporating any of the disclosed inventive features. The exact nature of the implant will vary according to the use desired. The implant can comprise mature tissue or can include immature tissue or the lattice. Thus for example, an implant can comprise a population of cells that are undergoing differentiation, optionally seeded within a lattice of a suitable size and dimension. Such an implant is injected or engrafted within a host to encourage the generation or regeneration of mature tissue within the animal.

The adipose-derived lattice is conveniently employed as part of a cell culture kit for use in animals. Accordingly, the invention provides a kit including adipose-derived lattice and one or more other components, such as hydrating agents (e.g. water, physiologically-compatible saline solutions, prepared cell culture media, serum or combinations or derivatives thereof), cell culture substrates (e.g. dishes, plates vials etc), cell culture media (whether in liquid or powdered form), antibiotics, hormones and the like. While the kit can include any such ingredients, preferably it includes all ingredients necessary to support the culture and growth of the desired cells upon proper combination for uses in an animal. The desired kit can also include cells which are seeded into the lattice as described.

The present invention now is described more fully by the following examples. This invention may, however, be embodied in many different forms and should not be construed as limited to the embodiments set forth herein; rather, these embodiments are provided so that this disclosure is thorough and complete, and fully conveys the scope of the invention to those skilled in the art.

EXAMPLES

Example 1

In Vitro Combination of Isolated Adipose Tissue-Derived Stem Cells with a Viscous, Liquid Phase Biomaterial Adipose-derived adult stem cells are isolated from liposuction waste material as described (Halvorsen, et al, Metabolism 2001, 50:407–413; Sen, et al. Journal of Cellular Biochemistry 2001, 81:312–319). The stem cells are expanded and suspended in a viscous, liquid phase biomaterial which is capable of gelling at body temperature and where the biomaterial includes, but is not limited to, alginate, collagen, fibrin, hyaline, plasma, or some other material. The suspension is at concentrations of 1 to $100 \times 10^6$ cells/ml [Erickson et al Biochemical & Biophysical Research Communications 2002, 290:763–9]. The biomaterial/stem cell suspension is permitted to gel at room temperature or 37°. The resulting cell matrix is maintained in growth media for periods of 1 day to 4 weeks.

During the culture period, conditioned media is analyzed using commercially available radio-immunoassays, enzyme-linked immunosorbent assays or radiolabeled biochemical assays for the expression of secreted proteins (Erickson et al Biochemical & Biophysical Research Communications 2002, 290:763–9).

Expression of phenotypic markers associated with chondrogenic differentiation is assessed by analysis of mRNA by RT-PCR using specific primers for the following (but not limited to) genes: collagen type II, collagen type VI, aggrecan, proteoglycan link protein. The presence of these markers and their association with chondrogenic cells has been previously described (Erickson et al Biochemical & Biophysical Research Communications 2002, 290:763–9). Immunohistochemical (IHC) analysis will also be performed using antibodies against any of the above described phenotypic markers according to methods previously described [Erickson et al Biochemical & Biophysical Research Communications 2002, 290:763–9].

Example 2

In Vitro Combination of Isolated Adipose Tissue-Derived Stem Cells with a Malleable Biocompatible Three-Dimensional Matrix The adipose tissue-derived stem cells in their undifferentiated or differentiated states can be combined with a malleable biocompatible three-dimensional matrix capable of filling an irregular cartilage fracture defect where the biocompatible material includes, but is not limited to, PGLA, PG, PL, or any other woven suture-like material.

Adipose-derived adult stem cells are isolated from liposuction waste material as described (Halvorsen, et al, Metabolism 2001, 50:407–413; Sen, et al. Journal of Cellular Biochemistry 2001, 81:312–319). The stem cells are expanded ex vivo and harvested by trypsin digestion and prepared as a single cell suspension at concentrations of 1 to $100 \times 10^6$ cells/ml in media as described [Erickson et al Biochemical & Biophysical Research Communications 2002, 290:763–9] or as a suspension in a viscous, liquid phase biomaterial capable of gelling at body temperature as described in Example 1 above. A solid, woven biomaterial such as Vicryl™ is "teased" out into an unwound tangle of single fibers with physical properties and consistency resembling that of a cotton ball. The stem cell suspension in media or in the viscous biomaterial is adsorbed onto the unwet or wet tangle of fibers by direct application. The resulting cell/biomaterial scaffold is maintained at 37° in growth media for periods of 1 day to 4 weeks according to published techniques [Erickson et al Biochemical & Biophysical Research Communications 2002, 290:763–9].

During the culture period, conditioned media is analyzed using commercially available radio-immunoassays, enzyme-linked immunosorbent assays or radiolabeled biochemical assays for the expression of secreted proteins.

Expression of phenotypic markers associated with chondrogenic differentiation is assessed by analysis of mRNA by RT-PCR using specific primers for the following (but not limited to) genes: collagen type II, collagen type VI, aggrecan, proteoglycan link protein. The presence of these markers and their association with chondrogenic cells has been previously described (Erickson et al Biochemical & Biophysical Research Communications 2002, 290:763–9). Immunohistochemical (IHC) analysis will also be performed using antibodies against any of the above described phenotypic markers according to methods previously described [Erickson et al Biochemical & Biophysical Research Communications 2002, 290:763–9].

Example 3

Other In Vivo Combinations of Adipose Tissue-Derived Stem Cells with Viscous Liquid or Malleable Biomaterials The adipose tissue-derived stem cells in their undifferentiated or differentiated states are combined with either a viscous liquid biomaterial and/or a malleable biocompatible three-dimensional matrix and a metal, plastic, or other biocompatible solid anchor and then transfixed into the cancellous bone underlying an articular cartilage fracture defect. The cells may be of either autologous or allogeneic in origin.

An articular cartilage fracture model is prepared in an appropriate mammalian species (dog, pig, goat, sheep) according to published methods [Trumble, et al, J Orthop Trauma, 2001, 15:326]. Animals are anesthetized and defects created in the knee according to an IACUC approved protocol designed to achieve equal and reproducible forces on the proximal tibial articular cartilage [Trumble, et al, J Orthop Trauma, 2001, 15:326]. Within the cartilage fracture site, the orthopedic surgeon will set metal multi-phallanged anchors topped with a single eyehook (purchased from Mytech or equivalent product) at 1 to 3 cm distances apart within the crevices between intact cartilage. The multi-phallanged anchors are drilled into the underlying cancelous bone. A suture is placed through the eyehooks of each anchor. The suture material such as Vicryl™ is "teased" out into an unwound tangle of single fibers with physical properties and consistency resembling that of a cotton ball in Examples 1 and 2 above. The tangle of fibers is used to fill in any crevices, fractures or fissures within the articular cartilage.

Adipose-derived adult stem cells are isolated from liposuction waste material or harvested adipose tissue as described (Halvorsen, et al, Metabolism 2001, 50:407–413; Sen, et al. Journal of Cellular Biochemistry 2001, 81:312–319). The cells used may be autologous, allogeneic or, in appropriate animal species and under selected circumstances, xenogenic. The stem cells are expanded and suspended in media or a viscous, liquid phase biomaterial at concentrations of 1 to $100 \times 10^6$ cells/ml as described in Examples 1 and 2 [Erickson et al Biochemical & Biophysical Research Communications 2002, 290:763–9]. The cell suspension is adsorbed onto the tangle of fibers by direct application. The biomaterial/stem cell suspension is permitted to gel at body temperature or 37°. The trauma sites will closed according to acceptable orthopedic surgical practice. After periods of 3 months to 12 months, animals are sacrificed and the defect sites evaluated for healing based on gross morphologic examination, histochemical, and immunohistochemical analyses.

Example 4

Genetic Modification of The Adipose Tissue-Derived Stem Cells and Their Use in Correcting Articular Cartilage Defects The procedure in Example 3 can be modified to employ adipose tissue derived stem or stromal cells that have been genetically modified to express any exogenous DNA. Exogenous DNA sequences include, but are not limited to, constitutively active bone morphogenetic proteins receptors, bone morphogenetic proteins [Sanyal, et al, J Orthop Res, 1999, 17:926–34], vascular endothelial growth factor and/or platelet derived growth factor [Richardsdn et al, Nat Biotechnol, 2001, 19:1029–34]. These exogenous DNA sequences are introduced into the adipose tissue derived stem or stromal cells by any of a number of methods, including but not limited to, viral vectors (including but not limited to adenovirus, retrovirus, adeno-associated virus), liposomes, plasmids, and/or by incorporation of DNA into the biomaterial matrix itself. The exogenous DNA is used to accelerate or enhance the process of cartilage repair and/or be used to monitor the progress and success of the reparative process.

Modifications and other embodiments of the invention will become apparent to one skilled in the art to which this invention pertains having the benefit of the teachings presented in the foregoing descriptions and associated drawings. It is to be understood that the invention is not limited to the specific embodiments disclosed and that modifications and other embodiments are intended to be included within the scope of the appended claims.

We claim:

1. A composition comprising an isolated adipose tissue-derived adult stem cell differentiated to express at least one characteristic of a chondrocyte in combination with a viscous, biocompatible liquid material implanted into a host, wherein the host is in need of articular cartilage repair.

2. The composition of claim 1, wherein the biocompatible liquid is capable of gelling at body temperature.

3. The composition of claim 2, wherein the biocompatible liquid is selected from the group consisting of alginate, collagen, fibrin, hyaline, or plasma.

4. The composition of claim 1 in; combination with a malleable, three dimensional matrix capable of filling an irregular cartilage defect.

5. The composition of claim 4, wherein the matrix is selected from the group consisting of polyglycolic-polylactic acid, poly-glycolic acid, poly-lactic acid, or suture-like material.

6. A composition comprising an isolated adipose tissue-derived adult stem cell differentiated to express at least one characteristic of a chondrocyte and implanted into host, a malleable, three dimensional matrix capable of filling an irregular cartilage defect and a solid phase, and a biocompatible material of sufficient structural integrity to serve as an anchor within the cancellous bone underlying the articular cartilage defect.

7. The composition of claim 6, wherein the biocompatible material comprises an isolated adipose tissue-derived stem cell differentiated to express at least one characteristic of an osteoblast.

8. The composition of claim 7, wherein the isolated adipose tissue-derived stem cell differentiated to express at least one characteristic of an osteoblast is grown in a matrix in vitro prior to implantation.

9. The composition of claim 1, wherein the cell is human.

10. The composition of claim 1, wherein the cell is modified with a nucleic acid.

11. A method of treating an articular cartilage defect in a host comprising implanting an isolated adipose tissue-derived adult stem cell differentiated to express at least one characteristic of a chondrocyte.

12. The method of claim 11, wherein the isolated adipose tissue-derived adult stem cell is in combination with a viscous, biocompatible liquid material.

13. The method of claim 12, wherein the biocompatible liquid is capable of gelling at body temperature.

14. The method of claim 13, wherein the biocompatible liquid is selected from the group consisting of alginate, collagen, fibrin, hyaline, or plasma.

15. The method of claim 13 further comprising a malleable, three dimensional matrix capable of filling an irregular cartilage defect.

16. The method of claim 15, wherein the matrix is selected from the group consisting of polyglycolic-polylactic acid, poly-glycolic acid, poly-lactic acid, or suture-like material.

17. A method of treating an articular cartilage defect in a host comprising implanting a composition comprising an insolated adipose tissue-derived adult stem cell differentiated to express at least one characteristic of a chondrocyte, a malleable, three dimensional matrix capable of filling an irregular cartilage defect and a solid phase, biocompatible material of sufficient structural integrity to serve as an anchor within the cancellous bone underlying the articular cartilage defect.

18. The method of claim 17 wherein the biocompatible material comprises an isolated adipose tissue-derived stem cell differentiated to express at least one characteristic of an osteoblast.

19. The method of claim 18 wherein the isolated adipose tissue-derived stem cell differentiated to express at least one characteristic of an osteoblast is grown in an matrix in vitro prior to implantation.

* * * * *